US006638289B1

(12) United States Patent
Johnson et al.

(10) Patent No.: US 6,638,289 B1
(45) Date of Patent: *Oct. 28, 2003

(54) ELONGATED ENDOSCOPIC CUTTING ACCESSORIES

(75) Inventors: Eric T. Johnson, Campbell, CA (US); Barry J. Kauker, Soquel, CA (US)

(73) Assignee: Stryker Corporation, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/688,467

(22) Filed: Oct. 16, 2000

(51) Int. Cl.⁷ .............................................. A61B 17/32
(52) U.S. Cl. ........................................ 606/170; 606/180
(58) Field of Search ........................... 606/1, 108, 170, 606/171, 180; 604/22

(56) References Cited

U.S. PATENT DOCUMENTS

| 219,252 | A | | 9/1879 | Bogoff | |
|---|---|---|---|---|---|
| 4,011,869 | A | | 3/1977 | Seiler, Jr. | |
| 4,203,444 | A | | 5/1980 | Bonnell et al. | |
| 4,923,441 | A | * | 5/1990 | Shuler | 606/170 |
| 5,269,794 | A | * | 12/1993 | Rexroth | 606/170 |
| 5,269,798 | A | * | 12/1993 | Winkler | 606/170 |
| 5,405,348 | A | * | 4/1995 | Anspach, Jr. et al. | |
| 5,437,630 | A | * | 8/1995 | Daniel et al. | 604/22 |
| 5,922,003 | A | * | 7/1999 | Anctil et al. | 606/170 |
| 5,961,532 | A | * | 10/1999 | Finley et al. | 606/170 |
| 6,068,641 | A | | 5/2000 | Varsseveld | 606/170 |
| 6,132,448 | A | | 10/2000 | Perez et al. | 606/180 |

FOREIGN PATENT DOCUMENTS

| EP | 0557044 | 8/1993 | ........... A61B/17/32 |
|---|---|---|---|
| GB | 2093353 | 9/1982 | ........... A61B/17/16 |
| WO | WO 9316648 | 9/1993 | ........... A61B/17/32 |

OTHER PUBLICATIONS

Endius MDS™ MicroDebrider System Pricelist and Product Description, Oct., 1998.
Assembly drawing for Stryker Cutter Housing Part No. 105–186–674 dated Feb. 1999.
Search Report for European Patent Application No. 01308812, Jan., 2002.

* cited by examiner

*Primary Examiner*—Carl Layno
(74) *Attorney, Agent, or Firm*—Flynn, Thiel, Boutell & Tanis, P.C.

(57) ABSTRACT

An elongated cutting accessory for performing endoscopic surgery. The accessory includes an inner tube to which a cutting member is attached and an outer tube that encases the inner tube. The outer tube may have first and second proximal and distal sections that are arranged end to end. The inner and outer diameters of the proximal section of the outer tube are greater than the corresponding diameters of the adjacent distal end section. An annular gap separates the outer surfaces of the inner tube with the inner surfaces of the outer tube. Irrigation fluid can be flowed through this gap. In some versions of the invention, two spaced apart hearing sleeves extend between the inner and outer tube. The distal of the two sleeves is formed with a channel through which the irrigation fluid can flow to a distal end opening in the outer tube.

45 Claims, 8 Drawing Sheets

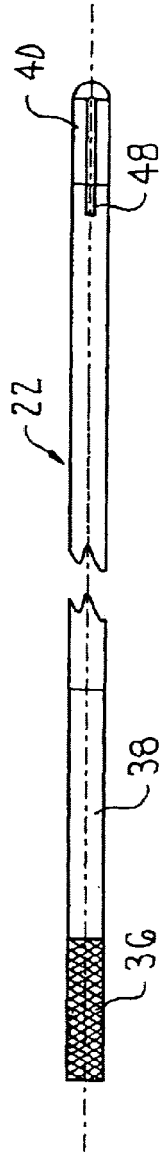
FIG. 2C
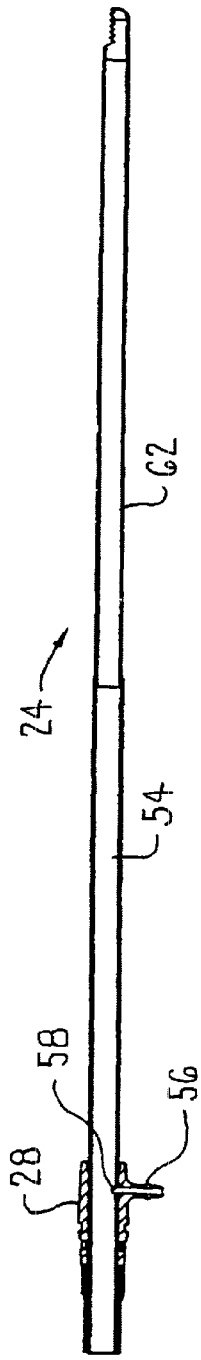
FIG. 3
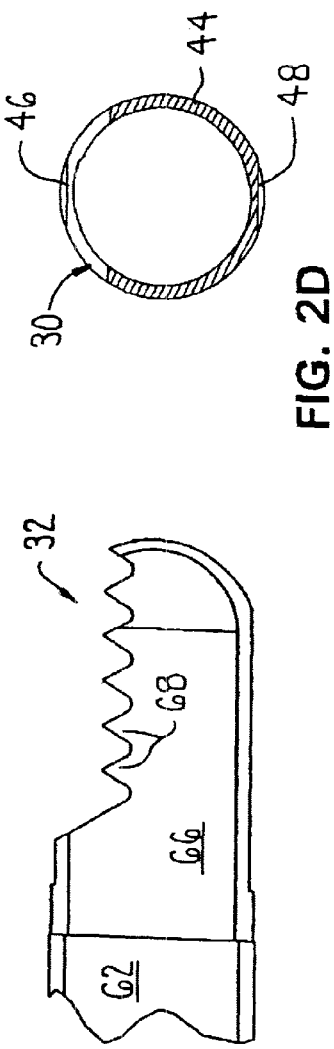
FIG. 2D
FIG. 4

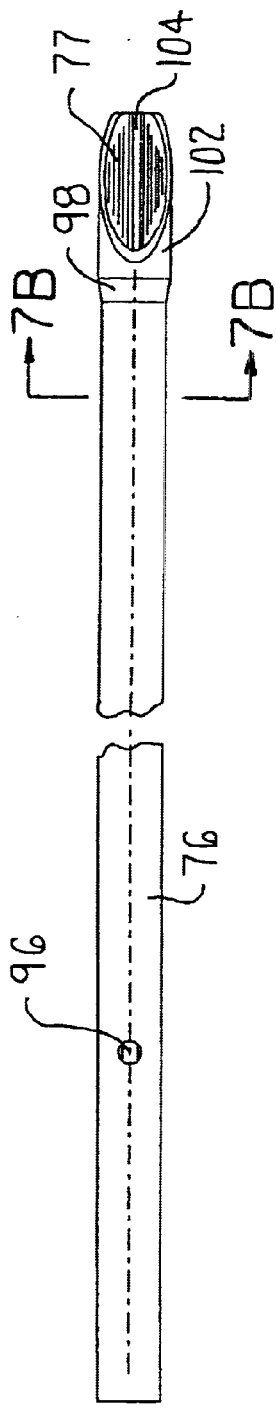
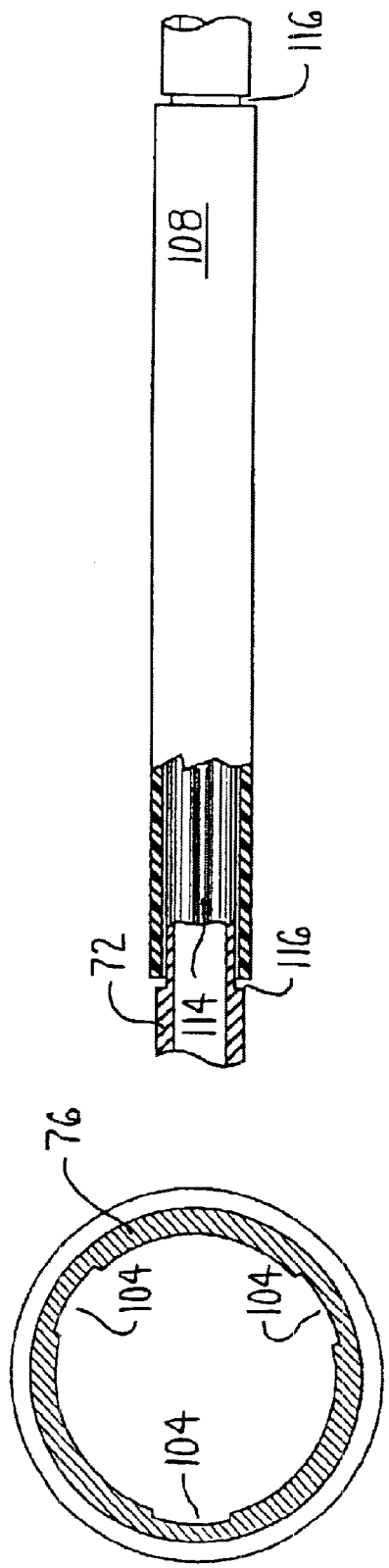
FIG. 7A
FIG. 7B
FIG. 8A

ELONGATED ENDOSCOPIC CUTTING ACCESSORIES

FIELD OF THE INVENTION

This invention relates generally to cutting accessories used with powered surgical handpieces to perform endoscopic surgical procedures. More particularly, this invention relates to elongated cutting accessories that are especially useful for performing surgical procedures at difficult to reach surgical sites such as the forward facing, anterior region, of the spine.

BACKGROUND OF THE INVENTION

Today, it is common that when a surgical procedure needs to be performed at a surgical site within the body of a living being that the procedure be performed endoscopically. In an endoscopic surgical procedure, an endoscope is placed in the surgical subject and positioned at the site at which it is necessary to perform the procedure. Other surgical instruments are also positioned at the surgical site. The endoscope and the other instruments are positioned in the body of being through small openings, called portals. The surgeon views the surgical site through the endoscope to determine how to manipulate the other surgical instruments in order to perform the desired surgical procedure. In an endoscopic procedure only the relatively small portals are formed in the body. Therefore, such a procedure is often referred to as minimally invasive surgery. This is unlike a conventional surgical procedure in which a relatively large incision is often made in order to gain access to the surgical site. One advantage of performing endoscopic surgery is that since the portions of the body that are cut are reduced, the portions of the body that need to heal after the surgery are likewise reduced. Still another advantage of endoscopic surgery is that it exposes less of the interior tissue of the body to the open environment. This minimal opening of the body lessens the extent to which its internal tissue and organs are open to infection.

The ability to perform endoscopic surgery has been made possible, in part, by the availability of surgical instruments especially designed to perform this type of surgery. An endoscopic surgical instrument typically has an elongated body. One end of the body, often referred to as the distal end, is designed to be positioned at the surgical site. The opposed end of the body, referred to as the proximal end, extends out of the body. The distal end of the body is provided with some type of working head designed to manipulate the tissue against which it is placed. The proximal end of the body is provided with a mechanism for controlling the working head.

Some endoscopic surgical instruments are designed for use with motorized handpieces. Often, these instruments are called "cutting accessories". These accessories typically include an elongated tube that forms the body of the accessory. The proximal end of the tube is provided with a hub used to releasably couple the tube to the motor rotor integral with the handpiece so that the tube rotates with the actuation of the motor. One type of cutting accessory is the bur. This accessory has a solid head; it is designed to selectively shape tissue, typically bone, against which it is placed. Other cutting accessories have drill heads that are used to bore into bone. Another type of endoscopic cutting accessory is the shaver. The shaver has a head with cutting edges. The shaver is used to selectively remove soft tissue from a surgical site. Many cutting accessories, in addition to having first, inner tubes that transmit rotational power, have second, outer tubes. The outer tube extends around the inner tube and is releasably held in a static position to the complementary handpiece. The outer tube serves as a shield that prevents tissue adjacent the cutting accessory from becoming entrained around the rotating inner tube. Moreover, the distal end of the outer tube that forms part of a shaver often has its own cutting edge. The moving cutting edge of the rotating inner tube and the static cutting edge of the outer tube form a scissors-like assembly that cooperate to cut the tissue against which the distal end of the shaver is pressed.

In order for it to be possible to perform endoscopic surgery, it is often necessary to supply irrigating fluid to and remove fluid from the surgical site. The simultaneous introduction of fluid to and removal of the fluid flushes debris, such as the severed tissue, away from the site. This enables the surgeon to have a clear view of the site. The introduction of the fluid also serves to expand, distend, the tissue in the vicinity of the site. This separation of tissue clears the field of view at the surgical site. Many powered handpieces and their complementary cutting accessories are provided with conduits designed to facilitate the introduction of fluid to and suction of fluid and debris from the surgical site. Specifically, often the inner and outer tubes of a cutting accessory are collectively dimensioned so that there is a small annular gap between the two tubes. This gap serves as the channel through which irrigation fluid is flowed through the outer tube and out the open distal end of this tube. The center of the inner tube typically serves as the suction conduit through which fluid and debris are drawn away from the surgical site. The distal end of this tube is provided with an opening. The hub at the end of this tube has an opening through which the tube is placed in fluid communication with a suction bore formed in the handpiece. A suction pump draws fluid and debris away from the surgical site through the distal end opening of the inner tube, the body of the inner tube, the tube hub, and the handpiece suction bore.

The development of elongated cutting accessories is one of the reasons why it has become possible to perform more surgical procedures endoscopically. To date, however, it has been difficult to provide relatively long endoscopic cutting accessories for powered surgical tools. This is because a cutting accessory is exposed to significant side loading forces when it is pressed against a surgical site in order to perform a surgical procedure. These forces flex the tubes forming the accessory. If the flexing is significant, the middle section of the inner tube may start to rub against an adjacent surface of the outer tube. This contact becomes a braking action, which can significantly slow or stop the rotation of the inner tube. The extent of the contact between these surfaces increases with the lengths of the accessory's tubes. In particular, the problems associated with side loading can start to affect the performance of the cutting accessory once the length of the cutting accessory exceeds 7.8 inches.

Some solutions have been proposed to minimize the extent of the bending problems associated with long-length cutting accessories. These solutions include increasing the wall thickness of the material forming these tubes. One disadvantage of this solution is that the size of the irrigation and/or suction channels formed by these tubes decrease. If not enough fluid can be introduced into and/or removed from a surgical site through the cutting accessory, additional portals must be formed in body in order to serve as access ports for fluid flow paths. Also, increasing the thickness of the tube walls may make it necessary to increase the size of the portals that lead to the surgical site. Alternatively, one could possibly manufacture the tubes forming these cutting accessories out materials that are better able to be subjected to side loading without bending. However, taking this action can significantly increase the cost of providing these accessories.

Since many long-length endoscopic cutting accessories are not readily available, it has proven difficult to perform endoscopic surgical procedures at certain surgical sites that are significantly spaced from the outer surface of the body.

SUMMARY OF THE INVENTION

This invention relates generally to the structure of cutting accessories intended for use with powered surgical handpieces that are designed to perform endoscopic procedures. More specifically, this invention relates to the construction of cutting accessories that facilitates providing accessories that have a relatively long length.

BRIEF DESCRIPTION OF THE DRAWINGS

The invention is pointed out with particularity in the claims. The above and further features of the invention may be better understood by reference to the following detailed description and the accompanying drawings in which:

FIG. 2C is a bottom view of the distal end of the inner tube of FIG. 2A;

FIG. 2D is a cross-sectional view of the head piece of the inner tube taken along ling 2D—2D of FIG. 2B;

FIG. 3 is a cross sectional view of the outer tube assembly of the shaver of FIG. 1A;

FIG. 4 is an enlarged cross sectional view of the distal end of the outer tube assembly of FIG. 1A;

FIG. 7A is a top view of the outer tube of the bur of FIG. 5;

FIG. 7B is a cross sectional view of the outer tube taken along line 7B—7B of FIG. 7A;

FIG. 8A depicts an alternative bearing sleeve of this invention and how the bearing sleeve is mounted to the inner tube;

DETAILED DESCRIPTION

Figure 1A:
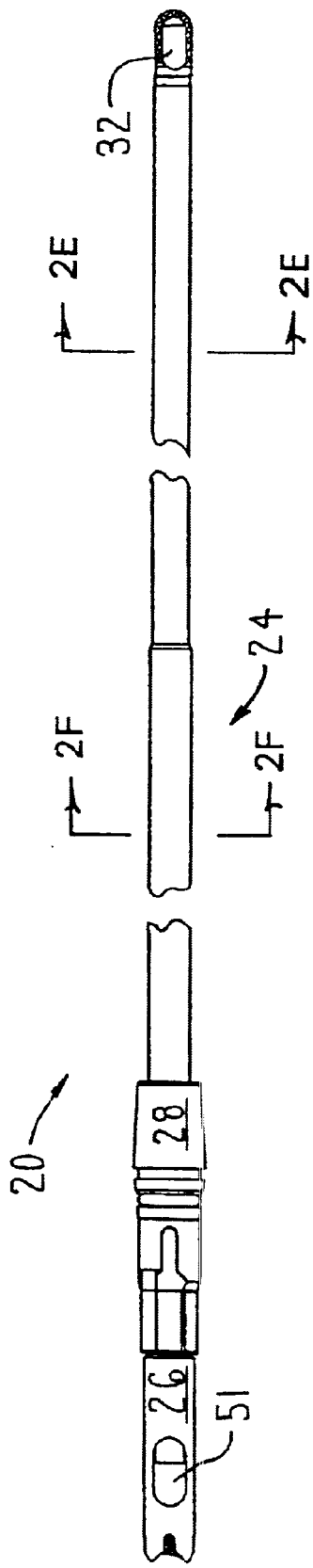
FIGS. 1A and 1B are, respectively, top and side views of one particular cutting accessory, a shaver, of this invention.
Figure 1B:
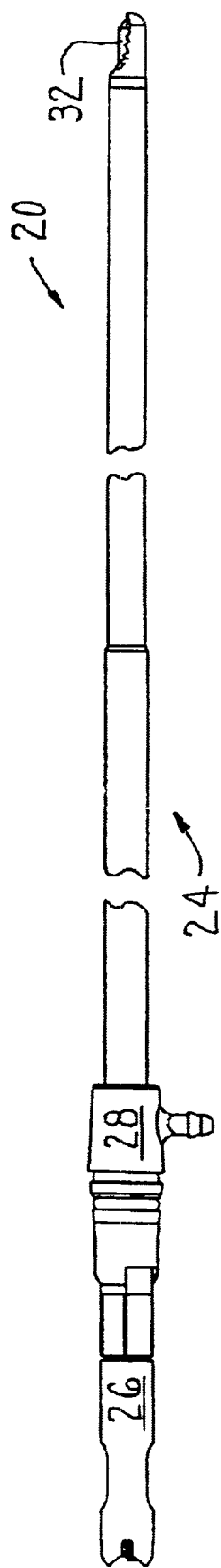
Figure 2A:
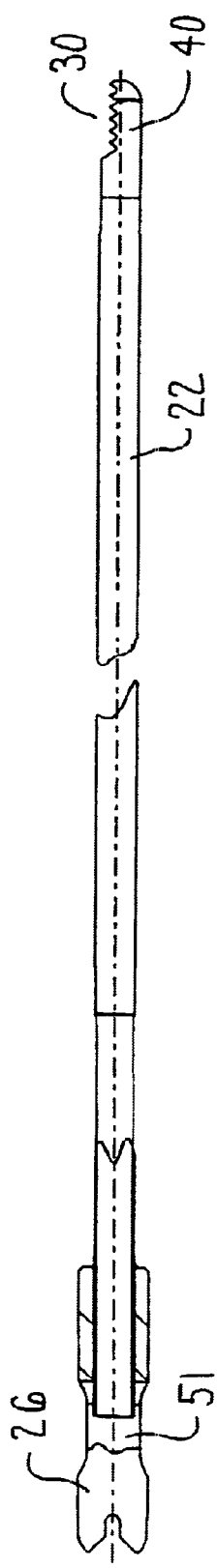
FIG. 2A depicts the inner tube of FIG. 1A and the components that are attached to the tube.

FIGS. 1A, 1B and 2A depict a particular cutting accessory, a shaver 20, of this invention. Shaver 20 includes an inner tube 22 that is substantially fitted within an outer tube assembly 24. Both inner tube 22 and the tubular elements of assembly 24 are formed from stainless steel or another material able to withstand medical sterilization processes. An inner hub 26 is fitted over the proximal end of the inner tube 22. ("Proximal" should be understood away from the surgical site to which the shaver 20 is applied.) An outer hub 28 forms the proximal end of outer tube assembly 24. The hubs 26 and 28 are designed to releasably couple the shaver 20 to a complementary handpiece that has a motor for actuating the shaver. One such handpiece is marketed by the Applicants' Assignee, the Stryker Corporation of Kalamazoo, Mich. as Part No. 275-701-500. The inner hub 26 releasably couples the inner tube 22 to an exposed rotor shaft of the handpiece so that the tube 22 rotates with the actuation of the handpiece motor. A coupling assembly integral with the handpiece engages the outer hub 28. The engagement of the outer hub 28 by the coupling assembly releasably holds the shaver 20 to the handpiece. The hubs 26 and 28 are typically formed out of plastic such as a polycarbonate plastic.

The distal end tips of both inner tube 22 and outer tube assembly 24 are closed. ("Distal" is understood to mean towards the surgical site to which the shaver 20 is applied.) Immediately proximal to the end tips, both tubes 22 and 24 have windows 30 and 32, respectively. The edge surfaces of the tubes 22 and 24 that define the windows 30 and 32, respectively, have sharp profiles. Thus, when the inner tube 22 is rotated relative to the outer tube, these edge surfaces cooperate to cut the tissue against which the distal end of the shaver 20 is pressed.

Figure 2B:
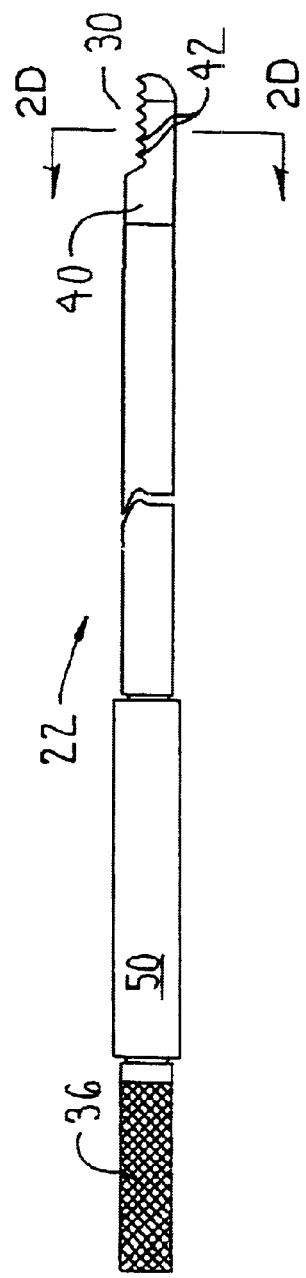
FIG. 2B is a side view of the inner tube of the shaver of FIG. 1A.

The inner tube 22 and the components integral therewith are now described by reference to FIGS. 2A, 2B and 2C. The inner tube 22, in most versions of the invention, has a length of 8.0 inches or more. In more preferred versions of the invention, tube 22 has a length 10.0 inches or more. In still more preferred versions of the invention, the inner tube has a length of 12.0 inches or more. In some versions of the invention, the outer diameter of the inner tube is between 0.15 and 0.20 inches. The thickness of the material forming the inner tube 22 is between 0.012 and 0.025 inches. The outer surface of the proximal end of inner tube 22 is formed as a knurled surface 36. The knurling facilitates the inductive welding of the tube 22 to the complementary inner hub 26. Spaced a slight distance forward of the surface 36, towards the distal end, inner tube 22 is formed to have a section 38 with a reduced diameter outer surface. In some versions of the invention, the outer diameter of section 38 is between 0.005 and 0.015 inches less than the outer diameter of the adjacent sections of the tube 22. The purpose for providing section 38 is described hereinafter.

In the depicted version of the invention, the actual distal end tip of the inner tube is a small closed end head piece 40 that is welded to the end of the body of the tube. Head piece 40 is formed to define tube window 30. In the depicted version of the invention, head piece 40 is shaped to have pointed teeth 42 that define window 30.

The head piece 40 and the adjacent distal end section of the open ended tube to which the head piece is attached are formed to have two flats 46 and 48, seen best in FIG. 2D. Flats 46 and 48 are formed along the outer surface of the head piece 40 and the adjacent tube section and a diametrically opposed from each other. Flat 46 extends proximally away from window 30. Flat 48 extends over the outer surface of the portion of the head piece 40 that defines window 30.

A bearing sleeve 50 is fitted over the reduced outer diameter section 38 of inner tube 22. In one version of the invention, bearing sleeve is a heat shrink FEP plastic. The bearing sleeve 50 is dimensioned so that when it is fitted and heat shrunk over the tube section 38, it has an outer surface that extends beyond the outer surfaces of the sections of the tube on either side of section 38. More particularly, when the shrunk bearing sleeve 50 and inner tube 22 sub-assembly are fitted in the outer tube assembly 24, the outer surface of the bearing sleeve abuts the adjacent inner surface of the outer tube so the sleeve forms a rotating seal between the two tubes. In FIG. 2B, and the other figures of this application, the relative difference in diameters between the bearing sleeves and the tubes to which they are attached is shown slightly exaggerated for purposes of illustration.

The inner hub 26 has an open-ended channel 51 that extends into the center of the inner tube 22. The channel 51 forms the flow path from the inner tube to the suction bore integral with the handpiece to which the shaver 20 is attached.

FIGS. 3 and 4 illustrate the components forming the outer tube assembly 24. Assembly 24 includes a first, upper tube 54. The upper tube 54 has an outer diameter of between 0.23 and 0.27 inches and a wall thickness of between 0.020 and 0.030 inches. While not illustrated, it should be understood that the proximal end of the upper tube is provided with knurling to facilitate the inductive welding of outer hub 28 to that end of the tube 54. The outer hub 28 is formed with an open-ended inlet spike 56 to which an irrigation fluid line can be coupled. The through bore integral with the inlet spike 56, (bore not identified) is in registration with a complementary bore 58 formed in upper tube 54. Thus, the inlet spike 56 and bore 58 collectively define the path through which irrigation fluid is introduced into upper tube 54.

Figure 2F:
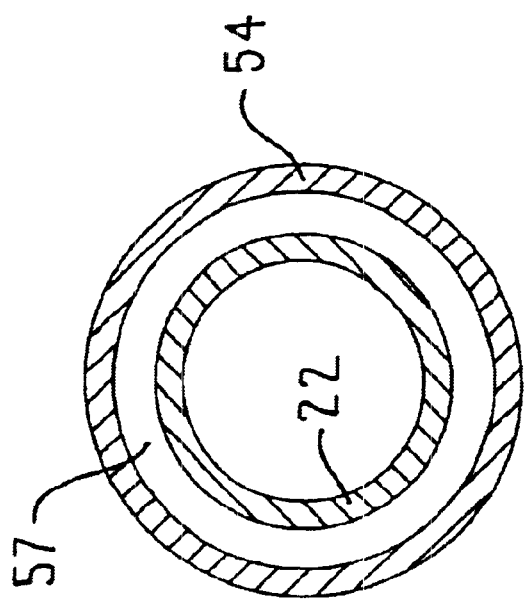
FIG. 2F is a cross sectional view through the cutting accessory of FIG. 1A taken along line 2F—2F.
Figure 2E:
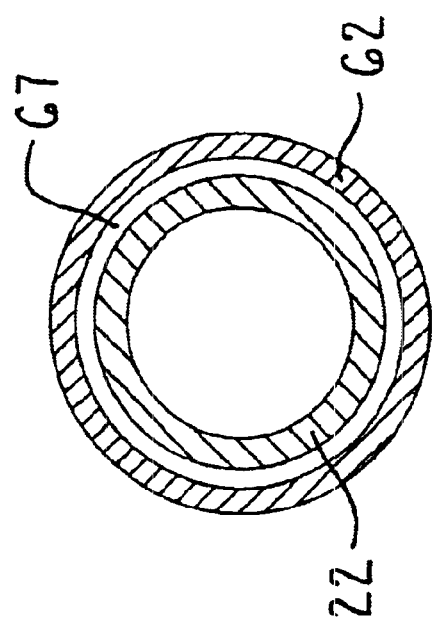
FIG. 2E is a cross sectional view through the cutting accessory of FIG. 1A taken along line 2E—2E.

A lower tube 62 is securely fitted to the open distal end of the upper tube 54. Lower tube 62 has an outer diameter of between 0.20 and 0.23 inches and a wall thickness of between 0.010 and 0.020 inches so as to define an annular gap 67, FIG. 2E, between tubes 22 and 62, through which the irrigation fluid flows. In order to facilitate the mating of the proximal end of the lower tube in the distal end of the upper tube 54, the distal end of the upper tube 54 is formed to have a counter bore (not illustrated) around its open distal end.

A head piece 66 fits over the open distal end of lower tube 62. The head piece 66 has an inner diameter that is approximately 0.005 and 0.015 inches smaller than the inner diameter of lower tube 62. The head piece defines window 32 of outer tube assembly 26. More particularly, the head piece 40 is formed with teeth 68 that define window 30. The head piece is further formed so that its section adjacent lower tube 62 has the same outer diameter as that of the lower tube. The more distal section of the head piece, the section in which window 30 is formed, has an outer diameter approximately 0.005 to 0.015 inches less than that of the lower tube 62.

When the shaver 20 is assembled, the distal end of inner hub 26 is spaced from the adjacent inner surface of the proximal end surface of outer hub 28 by approximately 0.015 inches. Tubes 22, 54 and 62 are dimensioned so that the head piece 40 integral with inner tube 22 abuts the inner radial surface of head piece 66 of the outer tube assembly 26. Inner tube teeth 42 and lower tube teeth 68 are adjacent each other and collectively define a cutting member at the end of the shaver 20. The bearing sleeve 50 abuts against and extends rearward of the portion of upper tube that extends proximally relative to tube bore 58.

One feature of cutting accessory 20 of this invention is that bearing sleeve 50 provides a low-friction interface between inner tube 22 and the adjacent section of the upper tube 54 of the outer tube assembly 24. This low-friction interface reduces the length of the cantilever arm formed by the inner tube 22. This arm thus starts at the distal end of bearing sleeve 50 and extends distally along the length of tube 22 to the closed end of headpiece 40. Thus, owing to the reduction in the length of this arm, when the shaver 20 is subjected to side loading, the extent to which the inner tube 22 is bent is reduced. Another feature of cutting assembly 20 is that, owing to the relatively wide inner diameter of upper tube 54, there is a relatively wide interstitial gap 57, FIG. 2F, between tubes 22 and 54, in comparison to the gaps between tubes 22 and 62. Specifically, this gap is between 0.010 and 0.020 inches. Thus, should the proximal end of the inner and upper tubes 22 and 54, respectively, be subjected to significant bending, the likelihood of these tubes bending to the extent that they abut is substantially reduced.

Collectively, the dual reduction in the side load bending of the inner tube 22 and the separation between inner and upper tubes 22 and 54, respectively substantially eliminates the likelihood that this contact between the tubes will occur. The elimination of this contact avoids the problems caused by such contact. Thus, even though the cutting accessory 20 of this invention is relatively long in length, it can be subjected to the significant side loading forces to which such accessories are exposed during endoscopic surgery. Given its length, this cutting accessory can be used to perform endoscopic surgery on difficult to reach body parts, such as the anterior region of the spine.

Still another feature of the invention is that bearing sleeve 50 also serves as a shock absorber that damps the vibration movement of the components forming the shaver 20. Also, the gap between tubes 22 and 54 serves as a reservoir for irrigation fluid. Once the irrigation pump that supplies this fluid is turned off, there is a brief period of time in which the fluid in this reservoir continues to flow out the distal end of the outer tube assembly 26. This supplemental fluid flow provides a last flush of debris that may still be present at the surgical site.

Figure 5:
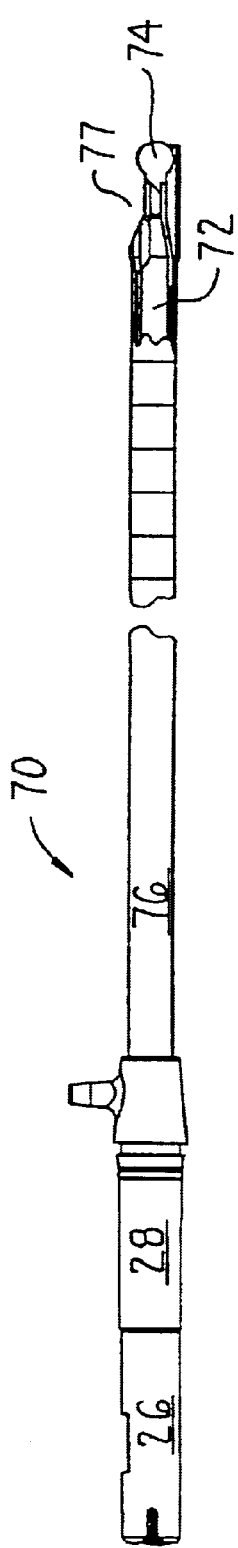
FIG. 5 is a side view of a second cutting accessory, a bur, of this invention, wherein the distal end of the outer tube is cutaway so that the distal end components of the inner tube can be observed.

A second cutting accessory of this invention, a bur 70, is now described by initial reference to FIG. 5. Bur 70 includes an elongated, hollow inner tube 72. A solid bur head 74 is securely attached to the distal end of the inner tube 72. An inner hub 26 is securely fitted to the opposed proximal end of the inner tube. Substantially all of the inner tube 72 is encased within a single piece hollow outer tube 76. The distal end of the outer tube 76 defines a side opening 77 through which the bur head 74 is exposed. An outer hub 28 is fitted to the proximal end of the outer tube 76.

Figure 6A:
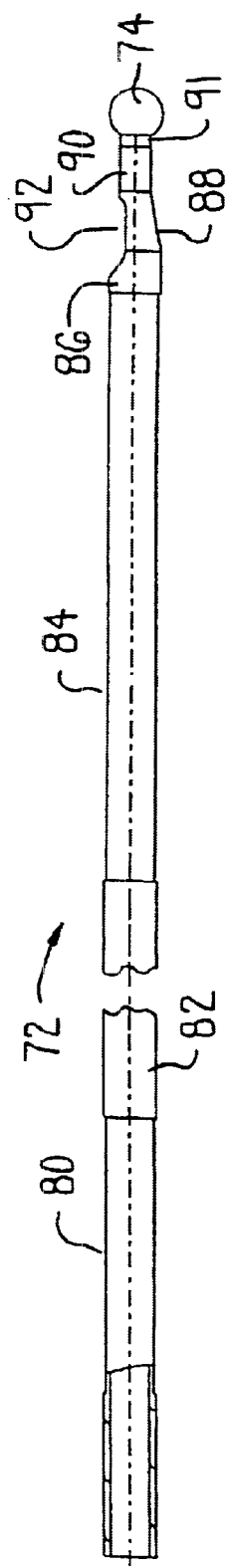
FIG. 6A is a side and partial cross sectional view of the inner tube of the bur of FIG. 5.
Figure 6B:
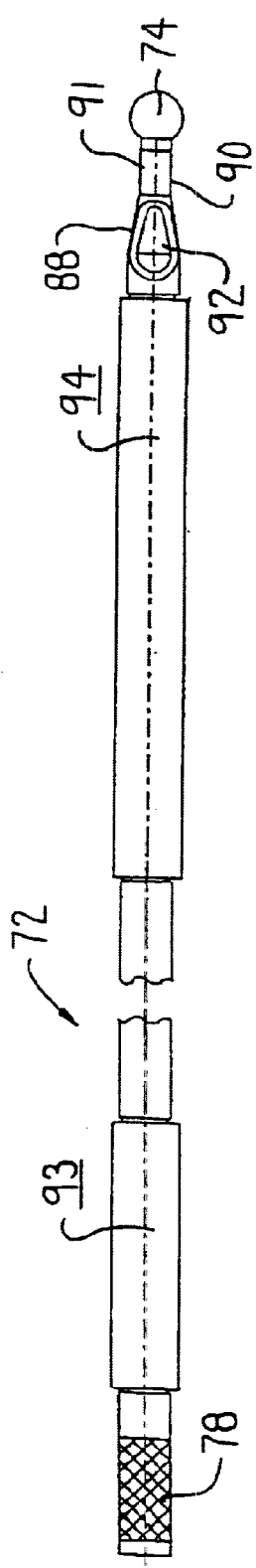
FIG. 6B is a side view of the inner tube of FIG. 6A in which the bearing sleeves that are mounted to the tube are illustrated.

The inner tube 72, as seen in FIGS. 6A and 6B is in the form of a single-piece, multi-section tube. The inner diameter of the tube is constant along the length of the tube. In some versions of the invention, the overall length of the tube, from the proximal end to the exposed distal end of the bur head 74, is at least 8.0 inches. In preferred versions of this invention, the overall length of the tube is at least 9.0 inches, in more preferred versions of the invention, the overall length of the tube is at least 10.0 inches. In still more preferred versions, the overall length is at least 11.0 inches. The outer diameter of the "full diameter" sections, the non-reduced diameter sections of the tube, is between 0.23 and 0.27 inches. The wall thickness of full diameter sections of the tube is between 0.020 and 0.035 inches. The proximal end section of the tube has the full diameter and is formed to have a knurled outer surface 78. Surface 78 is knurled to facilitate the inductive welding of the tube 72 and the inner hub 26 together. Immediately distal to surface 78, inner tube 72 is formed to have a reduced diameter section 80. The outer diameter of section 80 is approximately 0.005 to 0.020 inches less than the outer diameter of most sections of the tube.

Distal to section 80, inner tube 72 has a section 82 with a full diameter. Distal to section 82, the inner tube 72 is formed to have a second reduced diameter section, section 84. Section 84 has the outer diameter of section 80. The inner tube 72 is formed so that section 84 extends substantially the full length of the half of the tube located adjacent bur head 74. Specifically, when the overall length from the proximal end of the inner tube 72 to the distal end of the bur head 74 is 11.7 inches, section 84 extends approximately 2.0 to 6.0 inches along the length of the tube. In more preferred versions of this embodiment of the invention, section 84 has an overall length of between 2.2 and 3.0 inches.

The inner tube 72 is formed so that distal to section 84 there is a small full diameter section 86. Extending distally from section 86, tube 72 has a shoulder section 88 that generally has an inwardly tapered, frusto-conical profile. A constant diameter neck 90 extends distally from the end of shoulder section 88. A stem 91 integral with bur head 74 is fitted in neck 90 and secures the bur head to the inner tube 72.

Inner tube 72 is further formed to have a window 92 formed in its distal end. Window 92 is defined by portions of edge surfaces of the tube 72 that are within both section 86 and shoulder section 88. Window 92 serves an opening into the suction path defined by the center void through the tube 72 and the complementary opening in the inner hub 26.

First and second bearing sleeves 93 and 94, respectively, are securely fitted over the inner tube 72 as seen in FIG. 6B. First bearing sleeve 93 is fitted over reduced diameter section 80. The second bearing sleeve 94 is fitted over reduced diameter section 84. Bearing sleeves 93 and 94 are formed from the material from which sleeve 50 is formed. The bearing sleeves 93 and 94 are dimensioned so that, when secured over the inner tube 72, they have outer walls that extend beyond the outer walls of the full diameter sections of the tube 72. More particularly, the bearing sleeves 93 and 94 functions as rotating seals between inner tube 72 and outer tube 76.

As seen by FIGS. 7A and 7B, the outer tube 76 throughout substantially all of, but not entirely its length, has a substantially constant circular outer diameter. While not illustrated, the proximal end of outer tube 76 is formed with a knurled surface to facilitate the securement of the tube and outer hub 28 together. Distal of the proximal end of tube 76, the tube is formed with a bore 96. Bore 96 serves as a window through which irrigation fluid from hub inlet spike 56 can flow into the center of tube 76. The outer tube 76 is formed so that spaced slightly proximally from its distal end there is an outwardly flared neck 98. Distal from neck 98, the tube has a head section 102 with a constant outer diameter.

The diameter of head section 102 is greater than the diameter of the section of the tube located proximally of neck 98. The tube head section 102 is the portion of the tube 76 that is shaped to define the side opening 77 through which bur head 74 is exposed.

The inner wall of the outer tube 76 is substantially circular in cross sectional profile. The diameter of the tube is substantially constant along the length of the tube. The inner diameters of the tube neck 98 and head section 102 increase with the increasing outer diameters of these sections of the tube. The outer tube 76 is further formed to define four arcuately spaced apart, longitudinally extending grooves 104 in the inner wall. As seen in FIG. 7B, grooves 104 extend linearly between the proximal and distal ends of the tube 76.

When the bur 70 of this invention is assembled, inner tube 72 is seated in outer tube 76. The distal end of inner hub 26 abuts the adjacent proximal end of outer hub 28. Collectively, the components of bur 70 are dimensioned so that bearing sleeves 93 and 94 abut the adjacent inner wall of the outer tube 76. Also, the bur head 74 is seated in the outer tube head section 102.

The bur 70 of this invention is used like a conventional endoscopic cutting accessory bur. Once the complementary handpiece motor to which the bur is attached is actuated, the rotational power of the motor is transferred through inner hub 26 and tube 72 to bur head 74. The bur head 74 is placed against the tissue or bone in order to remove this material.

Collectively, sleeves 93 and 94 inhibit the lateral movement of the sections of the inner tube 72 against which they rest relative to the outer tube 76. The restriction of this movement reduces the length of the cantilever arm formed by the inner tube 72. The reduction in the length of this arm reduces the extent to which the inner tube 72 bends relative to the outer tube 76 when it is subjected to side loading. Moreover, to the extent the inner tube 72 does bend or flex, the presence of bearing sleeve 94 prevents tube-to-tube contact from occurring. Thus, the problems associated with such contact are likewise eliminated. Bearing sleeves 93 and 94 also damp vibrational movement of the components forming the bur 70.

The bur 70 of this invention supplies irrigating fluid by the introduction of fluid into the bur through inlet spike 56 and outer tube opening 96. Distal to the proximal end of bearing sleeve 94, the sleeve abuts the inner surface of outer tube 76. The irrigating fluid is, however, able to flow in the inner tube grooves 104 around the bearing sleeve 94 and to the surgical site. Thus, the fact that bearing sleeve 94 is provided to eliminate the likelihood of tube-to-tube contact does not prevent the bur 70 of this invention from being able to supply irrigation fluid to a surgical site.

In sum, even though the bur of this invention is relatively long in length, it is able to withstand side loading and able to provide irrigating fluid to the surgical site to which it is applied. Thus, the bur of this invention can be used to perform endoscopic surgery on sites that cannot be reached by conventional length endoscopic cutting accessories.

Figure 8B:
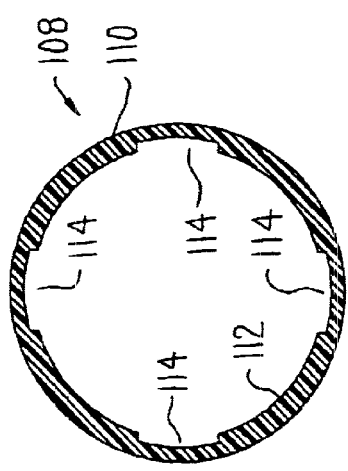
FIG. 8B is a cross sectional view of the bearing sleeve of FIG. 8A.

FIGS. 8A and 8B illustrate an alternative bearing sleeve 108 that can be fitted to inner tube 72 of bur 70. Sleeve 108 is formed to have a cylindrical outer wall 110. The sleeve 108 is further formed to have a generally circular inner wall 112 in which arcuately spaced apart grooves 114 are formed. Sleeve 108 is tightly fitted over reduced diameter section 84 of inner tube 72. The sleeve 108 is dimensioned so that that there are small annular interstitial gaps 116 between the ends of sleeve and the adjacent steps in the tube 72 that define the ends of section 84.

The outer tube with which the inner tube 72-and-sleeve 108 assembly is used may or may not be provided with grooves 104 along its inner wall.

The bur 70 with sleeve 108 is used in the same manner as the first described bur. When irrigation fluid is introduced into the annular gap between inner and outer tubes 72 and 76, respectively, the fluid flows into the gap 116 located adjacent the proximal end of sleeve 108. The fluid is able to flow through the sleeve 108 and, more particularly, through the grooves 114. Once the fluid flows through grooves 114, it flows through gap 116 adjacent the distal end of sleeve 84. From the distal end gap 116, the fluid flows out the end of the outer tube 76 in the conventional flow path.

Sleeve 108 can thus be provided in order to eliminate the need to provide the outer tube 76 with grooves. Alternatively, when tube 76 is formed with grooves 104, the grooves 114 of sleeve 108 increase the size of the flow path through which irrigation fluid can be discharged from the cutting accessory to the surgical site.

Figure 9A:
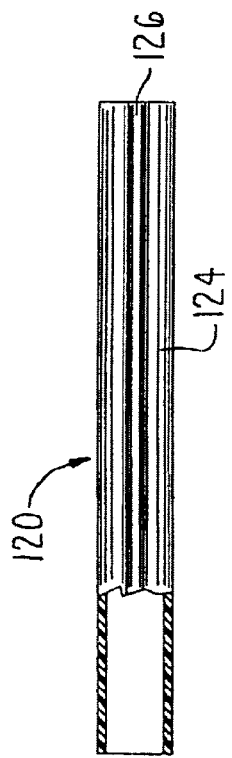
FIG. 9A is a longitudinal view of another alternative bearing sleeve of this invention.
Figure 9B:
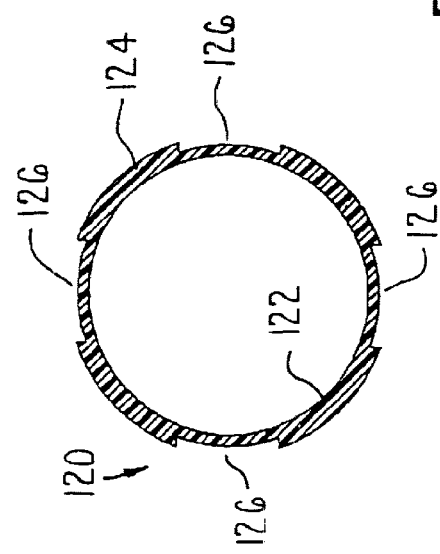
FIG. 9B is a cross sectional view of the bearing sleeve of FIG. 9A.

An alternative to sleeve 108, sleeve 120, is now described by reference to FIGS. 9A and 9B. Sleeve 120 is shaped to have a constant diameter circular inner wall 122. The outer wall 124 of sleeve 120 also has a circular shape. Sleeve 120 is further formed so that its outer wall 124 is further formed to have a plurality of angularly spaced apart recessed grooves 126.

An inner tube 72 to which sleeve 120 is attached is fitted in an outer tube 76 that has a smooth-surfaced inner wall. Grooves 126 serve as channels through which irrigation fluid is able to flow over the bearing sleeve 120.

Figure 10:
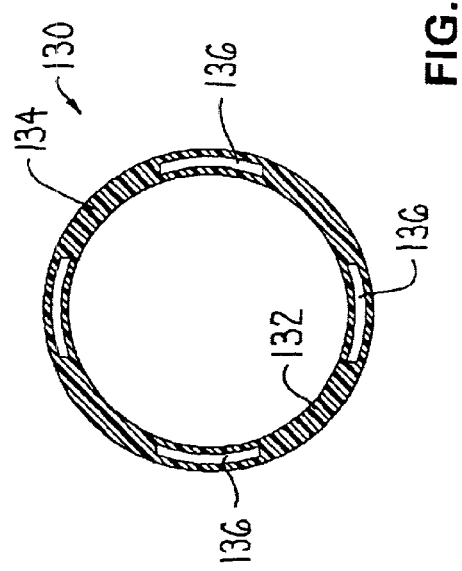
FIG. 10 is a cross sectional view of another bearing sleeve of this invention.

A second alternative to sleeve 108, sleeve 130, is illustrated in FIG. 10. Sleeve 130 is shaped to have inner and outer walls 132 and 134, respectively, that are both circular and smooth surfaced. The sleeve 130 is formed to have four internal channels 136 that are arcuately spaced apart from each other. Channels 136 extend the length of the sleeve 130 and are open at both ends of the sleeve.

An inner tube to which sleeve 130 is attached may be used with an outer tube 76 that is provided with grooves 104 or an outer tube with a smooth surfaced inner wall. When irrigation fluid is introduced into the outer tube 76, the fluid will flow through channels 136 and out the open end of the tube.

Figure 11:
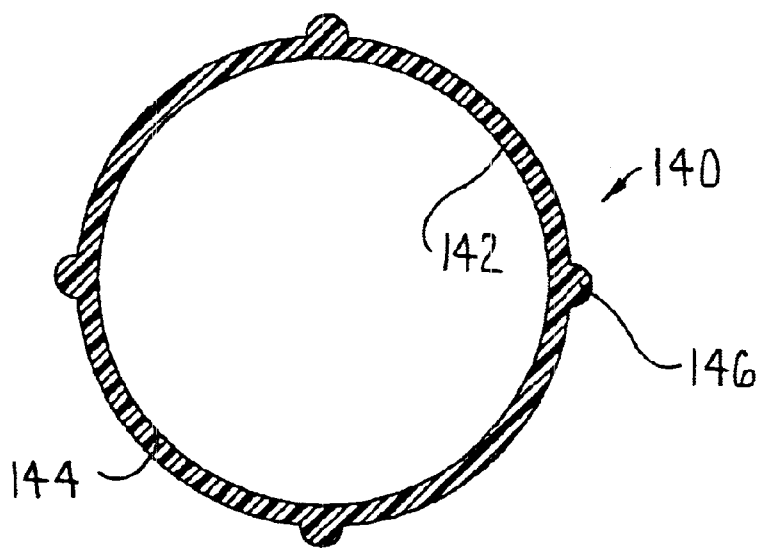
FIG. 11 is a cross sectional view of another bearing sleeve of this invention.

FIG. 11 depicts a third alternative to sleeve 108, sleeve 140. Sleeve 140 has inner and outer walls 142 and 144, respectively. The sleeve 140 is shaped so that inner wall 142 abuts the adjacent outer surface of inner tube 72 and outer wall 144 is spaced from the inner surface of outer tube 76. Sleeve 140 is further formed to have a number of equiangularly spaced-apart ribs 146 that project outwardly from outer wall 144. The sleeve 140 is formed so that ribs 146 abut the inner surface of the outer tube 76.

The ribs 146 thus serve as the members of sleeve 140 that provide the low friction interface between the inner and outer tubes 72 and 76, respectively. Since the surface contact between the ribs 146 and the outer tube is relatively minimal, this contact does not significant impede the rotation of the inner tube 72 relative to the outer tube 76. When irrigation fluid is introduced into the bur 70 of this embodiment of the invention, the fluid flows over the outer wall 144 of the sleeve 140, in the arcuate spaces between the ribs 146.

Figure 12:
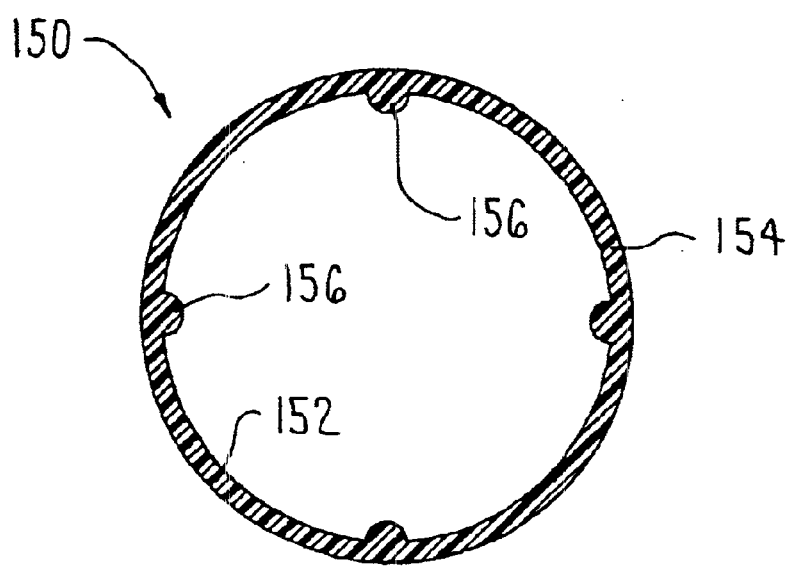
FIG. 12 is a cross sectional view of another bearing sleeve of this invention.

Sleeve 150, another alternative to sleeve 108, is now described by reference to FIG. 12. Sleeve 150 has inner and outer walls 152 and 154, respectively. Equiangularly spaced apart ribs 156 extend inwardly from the inner wall 152. When a bur 70 with sleeve 150 is assembled, the outer wall 154 abuts the adjacent inner surface of outer tube 76. Ribs 156 press against the inner surface of inner tube 72 and suspend the sleeve inner wall 152 away from the inner tube.

During use of the bur 70, sleeve outer wall 154 is the rotating interface between the rotating components and the fixed components of the bur. Irrigation fluid flows in the arcuate interstitial spaces between the ribs 156, the sleeve inner wall 152 and the adjacent outer surface of inner tube 72.

It should be realized that the foregoing description is directed to specific versions of the invention. It should be understood that the disclosed shapes of the shaver windows 30 and 40 and bur head 74 are exemplary. In other versions of the invention these features may have different forms. Also, the tubes forming this invention may be configured to form other cutting accessories such as resectors.

Moreover, in some versions of the invention, the disclosed features may be interchanged and/or combined. For example, in some versions of the invention, it may be desirable to provide burs with multi-section tube assembly 24. In this version of the invention, it may or may not be necessary to provide the bur inner tube with bearing sleeve that is fitted to the distal end of the tube. Similarly, in some versions of the invention, it may be desirable to provide a shaver or other cutting accessory with one of the bearing sleeves 94, 108, 120, 130, 140 or 150 in order to facilitate fluid flow out the end of the accessory.

Also, the particular construction of the inner and outer hubs 26 and 28, respectively, may vary with the type of handpiece with which the cutting accessory is intended to be used.

Clearly, the materials from which the described components are formed may vary from what has been described. Sleeves 108, 120 and 130, for example, may be formed from a hard, low friction fluorine resin plastic such as one marketed under the trademark TEFLON.

Similarly, while the outer tube 76 is shown as having three grooves 104 and sleeves 108, 120 and 130 are shown with four grooves or channels, this is exemplary. Other versions of these components may have fewer or more of these fluid-flow channels. Similarly, sleeve 140 and 150 are shown as each having four ribs 146 and 156, respectively. Again, this is merely exemplarily. In other versions of these sleeves few or more ribs may be provided. Also, in the described versions of the invention, each rib 146 and 156 is understood to be a unitary member that extends the longitudinal length of the sleeve with which the rib is integral. That need not always be the case. In some versions of the invention, the ribs may only extend a short distance along the length of their associated sleeve. The sleeve is further constructed so as to have ribs that are spaced apart from each other both radially around the sleeve and longitudinally along the length of the sleeve. Moreover, in these versions of the invention, the ribs may be arranged in a helical pattern around the associated sleeve.

Therefore, it is an object of the appended claims to cover all such modifications and variations that come within the true spirit and scope of the invention.

What is claimed is:

1. A cutting accessory for use with a powered surgical tool, said cutting accessory including:

an elongated inner tube having a proximal end and a distal end opposite the proximal end;

an inner hub attached to the proximal end of said inner tube;

a cutting member at least partially integral with the distal end of said inner tube;

an outer hub disposed over said inner tube and located forward of said inner hub, said outer hub shaped to be releasably held to a powered surgical tool, said outer hub being formed have an axially extending through bore, wherein said inner tube extends through the through bore, and a lateral bore that opens into the through bore;

an outer tube assembly, wherein said inner tube is at least partially disposed in said outer tube assembly, said outer tube assembly having: a first section that has a proximal end that is seated in the through bore of said outer hub and that extends forward from said outer hub and that extends over a proximal portion of said inner tube, the first section having first inner and outer diameters and being formed with an opening that is in registration with the end of the outer hub lateral bore that opens into the through bore; and a second section that is attached to and extends forward of said first section, the second section extending over a distal portion of said inner tube and having second inner and outer diameters, the second inner diameter being less than the first inner diameter, and the second outer diameter being less than the first outer diameter wherein said inner tube and said outer tube assembly are dimensioned so that said outer tube assembly first and second sections are spaced away from said inner tube; and a bearing sleeve fitted to said inner tube so as to extend from a position proximal to the opening in the first section of said outer tube assembly towards said inner hub so that at least a portion of said inner tube over which said outer tube first section extends is not covered by said bearing sleeve, said bearing sleeve providing an interface between said inner tube and the first section of said outer tube assembly.

2. The cutting accessory of claim 1, wherein:

said inner tube, including said portion of said cutting number integral with said inner tube, has a length of at least 10.0 inches; and said outer tube assembly is dimensioned and shaped so that the second section has a distal end that at least partially covers said cutting meter.

3. The cutting accessory of claim 1, wherein said inner tube is formed so that the distal end is closed and, adjacent the distal end, said inner tube is formed with a surface that is said cutting member.

4. The cutting accessory of claim 1, wherein, said inner tube has a first window located adjacent the distal end;

and the second section of said outer tube assembly extends over the distal end of said inner tube and is formed with a second window; and said inner tube has an edge surface that defines the first window and the second section of said outer tube assembly has an edge surface and the edge surfaces are collectively shaped to form said cutting member.

5. The cutting accessory of claim 1, wherein the first section and the second section of said outer tube assembly are formed, respectively, from separate first and second outer tube members that are attached together.

6. The cutting accessory of claim 1, wherein said cutting mentor is a bur attached to the distal end of said inner tube.

7. A cutting accessory for use with a powered surgical tool, said cutting accessory including:

an elongated inner tube having a proximal end, a distal end opposite the proximal end and an outer surface;

an inner hub attached to the proximal end of said inner tube;

a cutting member integral with the distal end of said inner tube;

an outer tube disposed over said inner tube and extending from said inner tube to over said cutting meter, said outer tube having a distal end that is at least partially open to expose said cutting member, an opening adjacent said inner hub for receiving fluid, and an inner surface wherein said inner tube and said outer tube are collectively dimensioned to define a gap between the outer surface of said inner tube and the inner surface of said outer tube;

a first bearing member secured to said inner tube to rotate with said inner tube and provide an interface between said inner tube and said outer tube, said first bearing member extending from said inner hub to a position proximal to the opening in Bald outer tube; and a second bearing member secured to said inner tube to rotate with said inner tube and provide an interface between said inner tube and said outer tube, said second bearing member extending from a position distal to the opening in said outer tube towards the distal end of said outer tube, wherein said second bearing member is formed with at least one channel through which fluid can flow past said second bearing member.

8. The cutting accessory of claim 7, wherein said inner tube and said cutting member collectively have a length of at least 10.0 inches.

9. The cutting accessory of claim 1, wherein said outer tube is formed so as to have at least one groove along the inner surface, the groove extending across said second bearing member.

10. The cutting accessory of claim 7, wherein said second bearing member has an outer surface and is formed to define at least one groove in the outer surface, the groove being the at least one channel of said second bearing member.

11. The cutting accessory of claim 7, wherein:

said outer tube is formed with a smooth walled inner surface that surrounds said second bearing member; and said second bearing member is formed to have a smooth walled outer surface so that the inner surface of said outer tube and the outer surface of said bearing member are in continuous contact around said second bearing member and said second bearing member has an inner surface that is formed to define at least one groove in the inner surface, the groove being the at least one channel of said second bearing member.

12. The cutting accessory of claim 7, wherein:

said outer tube is formed with a smooth walled inner surface that surrounds said second bearing meter; and said second bearing member is found to have a smooth walled outer surface so that the inner surface of said outer tube and the outer surface of said second bearing member are in continuous contact around said second bearing member and said second bearing member is formed to have an inner surface, and said at least one channel is an enclosed channel that extends longitudinally through said second bearing member and that is spaced from the inner and outer surfaces of said second bearing meter.

13. The cutting accessory of claim 7, wherein said cutting mentor is a bur head that is attached to the distal end of said inner tube.

14. The cutting accessory of claim 7, wherein said inner tube is formed to have a full diameter section that has a first outer diameter and first and second reduced diameter sections that have a second outer diameter, the second outer diameter being less than the first outer diameter, the first and second reduced diameter sections are spaced apart trot each other, said first bearing member is fitted over the first reduced diameter section and said second bearing member is fitted over the second reduced diameter section of said inner tube.

15. The cutting accessory of claim 7, wherein said inner tube is formed so as to have an opening in the distal end and a section of said inner tube that defines the opening is shaped to form said cutting member.

16. The cutting accessory of claim 7, wherein the distal end of said outer tube is shaped so as to be outwardly flared relative to adjacent sections of said outer tube.

17. A cutting accessory adapted for use with a powered surgical tool, said cutting accessory including:
   an cuter hub adapted to be releasably secured to the powered surgical tool, said outer hub having first and second opposed ends, an axially extending through bore that extends between the first and second ends and an inlet opening that extends from an outer surface to the through bore;
   an outer tube, said outer tube having first and second sections that are joined together end-to-end, the first section having an outer tube proximal end that is seated in the through bore of said outer hub and that extends from the second end of said outer hub and a bore that is spaced from the proximal end, the bore being in registration with the inlet opening of said outer hub, the second section having a circular cross sectional profile and an outer tube distal end that is spaced from the proximal end, the distal end being formed with an opening, wherein the sections of said outer tube have inner diameters and the inner diameter of the first section is greater than the inner diameter of the second section;
   an inner hub located adjacent the first end of said outer hub, said inner hub adapted to be releasably attached to a drive unit integral with the surgical tool:
   an inner tube having a length of at least 12.0 inches that is attached to said inner hub so as to rotate with said inner hub, said inner tube extending through said outer hub and into said outer tube, said inner tube having a distal end located adjacent the distal end of said outer tube and said outer tube first and second sections and said inner tube are shaped so that said outer tube sections are spaced from said inner tube;
   a cutting member, said cutting member at least partially integral with the distal end of said inner tube and being positioned to be located in registration with the opening in the distal end of said outer tube; and
   a bearing sleeve that is fitted to said inner tube and that is located over a section of said inner tube that is distal to said inner hub and proximal to the bore formed in the outer tube first section, said bearing sleeve extending between said inner and outer tubes.

18. The cutting accessory of claim 17, wherein,
   said inner tube has a first window located adjacent the distal end;
   the second section of said cuter tube extends over the distal end of said inner tube; and
   said inner tube has an edge surface that defines the first window and the second section of said outer tube has an edge surface that defines the opening in the distal end of said outer tube and said edge surfaces are collectively shaped to form said cutting member.

19. The cutting accessory of claim 17, wherein the first section of said outer tube has a first outer diameter and the second section of said outer tube assembly has a second outer diameter, the second outer diameter being less than the first outer diameter.

20. A cutting accessory for use with a powered surgical tool, said cutting accessory including:
   an outer hub adapted to be releasably secured to the powered surgical tool, said outer hub having first and second opposed ends, an axially extending through bore that extends between the first and second ends and an inlet opening that extends from an outer surf ace to the through bore;
   an outer tube, said outer tube having t a proximal end that is secured to the second end of said outer hub; a bore spaced from the proximal end, the bore being in registration with the inlet opening of said outer hub; a distal end opposite the proximal end; and an inner surface;
   an inner hub, said inner hub located adjacent the first end of said outer hub, said inner hub adapted to be releasably secured to a drive unit integral with the surgical tool;
   an inner tube that extends through said outer hub and said outer tube, said inner tube having a proximal end that is attached to said inner hub and a distal end adjacent the distal end of said outer tube;
   a cutting meter integral with the distal end of said inner tube;
   a first bearing meter fitted to said inner tube to rotate in unison with said inner tube, said bearing member being located over a section of said inner tube that extends from said inner hub and is proximal to the bore formed in said outer tube and dimensioned to extend between said inner and outer tubes;
   a second bearing member fitted to said inner tube to rotate in unison with said inner tube, said second bearing meter being spaced from said first bearing member and being located over a section of said inner tube that extends forward from the bore formed in said outer tube towards the distal end of said outer tube, and dimensioned to extend between said inner and outer tubes,
   wherein said second bearing member is formed with at least one channel through which fluid can flow past said second bearing meter.

21. The cutting accessory of claim 20 wherein said inner tube has a length of at least 10.0 inches.

22. The cutting accessory of claim 20, wherein said outer tube is formed so as to have at least one groove along the inner surface, the groove extending across said second bearing member.

23. The cutting accessory of claim 20, wherein:
   said outer tube is formed with a smooth walled inner surface that surrounds said second bearing member; and
   said second bearing meter is found to have a smooth outer surface so that the inner surface of said outer tube and the outer surface of said second bearing member and in continuous contact around said second bearing meter and said second bearing member baa an inner surface and is formed to define at least one groove in the inner surface, the groove being the at least one channel of said second bearing member.

24. The cutting accessory of claim 20, wherein:
said outer tube is formed with a smooth walled inner surface that surrounds said second bearing member; and
said second bearing member is formed to have a smooth walled outer surface so that the inner surface of said outer tube and the outer surface of said second bearing member are in continuous contact around said second bearing member; an inner surface, the inner surface being the surface of said second bearing member that abuts said inner tube; and said at least one channel is an enclosed channel that extends longitudinally through said second bearing sleeve and that is spaced from the inner and outer surfaces of said second bearing member.

25. The cutting accessory of claim 20, wherein said cutting member is a bur head that is attached to the distal end of said inner tube.

26. The cutting accessory of claim 20, wherein said inner tube is formed so as to have an opening in the distal end and a section of said inner tube that defines the opening is shaped to form said cutting member.

27. The cutting accessory of claim 20, wherein the distal end of said outer tube is shaped so as to be outwardly flared relative to adjacent portions of said outer tube.

28. The cutting accessory of claim 20, wherein:
said inner tube is formed to have an outer surface that is shaped to define two spaced apart recessed sections relative to adjacent sections of said inner tube, a first one of said recessed sections being disposed around a portion of said inner tubs subtended by said outer hub and a second one of said recessed sections being located distal to the bore formed in said outer tube; and
said bearing members are formed from a plastic material and said first bearing member is seated in the first recessed section formed in said inner tube and said second bearing member is seated in the second recessed section formed in said inner tube.

29. A cutting accessory adapted for use with a powered surgical tool, said cutting accessory including:
an inner hub, said inner hub adapted to be releasably attached to a drive unit integral with the tool;
an inner tube that is attached to said inner hub so as to extend from and rotate with said inner hub, said inner tube having an outer surface and a distal end spaced from said inner hub;
an outer hub fitted over said inner tube adjacent said inner hub, said outer hub adapted to be releasably secured to the powered surgical tool and being formed to define an inlet opening that is directed to a center axis of said outer hit;
an outer tube, said outer tube extending from said outer hub so as to be disposed over said inner tube, said outer tube having first and second sections that are joined together end-to-end,
the first section having a proximal end that is disposed within said outer hub and that extends forward from said outer hub and being disposed over a proximal section of said inner tube that is located adjacent said inner hub, the proximal end of said outer tube first section having an inlet bore that is in registration with the inlet opening of said outer hub and the first section of said outer tube has inner and outer diameters,
the second section being disposed over a distal section of said inner tube that is located adjacent the distal end of said inner tube and having inner and outer diameters, the inner diameter of the first section being greater than the inner diameter of the second section and the outer diameter of the first section being greater than the outer diameter of second section, the second section being shaped to have a distal end spaced from said outer hub with an opening,
wherein said inner tube and said outer tube are collectively dimensioned so as to define a first annular gap that that extends circumferentially around said inner tube between said inner tube and said outer tube first section and a second annular gap that extends circumferentially around said inner tube and said outer tube second section and so that the first annular gap has a width that is greater than the width of the second annular gap;
a cutting mentor, said cutting meter at least partially integral with the distal end of said inner tube and being positioned to be in registration with the opening in the distal end of said outer tube second section; and
a bearing sleeve that is fitted to said inner tube and that is located over a section of said inner tube that is distal to said inner hub and proximal to the inlet bore formed in said outer tube first section, said bearing sleeve extending between said inner and outer tubes.

30. The cutting accessory of claim 29, wherein:
said inner tube has a first window located adjacent the distal end;
the second section of said outer tube extends over the distal end of said inner tube and is formed with a second window, that functions as the opening in said outer tube second section; and
said inner tube has an edge surface that defines the first window and the second section of said outer tube assembly has an edge surface that defines the second window and the edge surfaces are collectively shaped to f on said cutting member.

31. The cutting accessory of claim 29, wherein said inner tube has a length of at least 10.0 inches.

32. The cutting accessory of claim 29, wherein said cutting member is a bur attached to the distal end of said inner tube.

33. A cutting accessory for use with a powered surgical tool, said cutting accessory including:
an elongated inner tube having a proximal end and a distal end opposite the proximal end and a cutting member at least partially integral with the distal end of said inner tube, said inner tube and said portion of said cutting member integral with said inner tube having a length of at least 10.0 inches;
an inner hub attached to the proximal end of said inner tube;
an outer hub disposed over said inner tube and located forward of said inner hub, said outer hub shaped to be releasably held to a powered surgical tool, said outer hub being formed with an axially extending through bore and a lateral bore that opens into the through bore;
an outer tube assembly, wherein said inner tube is at least partially disposed in said outer tube assembly, said outer tube assembly having: a first section that has a proximal end that is seated in the through bore of said outer hub and that extends forward from said outer hub and that extends over a proximal portion of said inner tube, the first section having a first inner diameter and being formed with an opening that is in registration with the outer end of the hub lateral bore; and a second section that is attached to said first section, the second section extending over a distal portion of said inner tube and having a distal end that at least partially covers said cutting member, the second section having a circular cross-sectional profile with a second inner diameter, the second inner diameter being less than the first inner diameter, wherein said inner tube and said outer tube assembly are dimensioned so that said outer tube assembly first and second sections are spaced away from said inner tube; and a bearing sleeve fitted to said inner tube so as to extend from a position proximal to the opening in the first section of said outer tube assembly towards said inner hub so that at least a portion of said inner tube over which said outer tube first section extends is not covered by said bearing sleeve, said bearing sleeve providing an interface between said inner tube and the first section of said outer tube assembly.

34. The cutting accessory of claim 33, wherein said inner tube, including said portion of said cutting member integral with said inner tube, has a length of at least 12.0 inches.

35. The cutting accessory of claim 33, wherein said inner tube is formed so that the distal end is closed and, adjacent the distal end, said inner tube is formed with a surface that is said cutting member.

36. The cutting accessory of claim 33, wherein:

said inner tube has a first window located adjacent the distal end;

the second section of said outer tube assembly extends over the distal end of said inner tube and is formed with a second window; and said inner tube has an edge surface that defines the first window and the second section of said outer tube assembly has an edge surface and the edge surfaces are collectively shaped to form said cutting member.

37. The cutting accessory of claim 33, wherein the first section of said outer tube assembly has a first outer diameter and the second section of said outer tube assembly has a second outer diameter, the second outer diameter being less than the first outer diameter.

38. The cutting accessory of claim 33, wherein the first section and the second section of said outer tube assembly are formed, respectively, from first and second outer tube members, each said outer tube member having an outer diameter, the outer diameter of said second tube member being less than the outer diameter of said first tube member.

39. The cutting accessory of claim 33, wherein said cutting member is a bur attached to the distal end of said inner tube.

40. A cutting accessory adapted for use with a powered surgical tool, said cutting accessory including:

an inner hub, said inner hub adapted to be releasably attached to a drive unit integral with the tool;

an inner tube that is attached to said inner hub so as to extend from and rotate with said inner hub, said inner tube having a circular outer surface and distal end spaced from said inner hub, said inner tube having a length of at least 10.0 inches;

an outer hub fitted over said inner tube adjacent said inner hub, said outer hub adapted to be releasably secured to the powered surgical tool and being formed to define an inlet opening that is directed to a center axis of said outer hub;

an outer tube, said outer tube extending from said outer hub so as to be disposed over said inner tube, said outer tube having first and second sections that are joined together end-to-end;

the first section being disposed over a proximal section of said inner tub that is located adjacent said inner hub and having an inlet bore, the inlet bore being in registration with the inlet opening of said outer hub, the second section being disposed over a distal section of said inner tube that is located adjacent the distal end of said inner tube and being shaped to have a distal end spaced from said outer hub with an opening, wherein said inner tube and said outer tube are collectively dimensioned so as to define a first annular gap that extends circumferentially around said inner tube between said inner tube and said outer tube first section and a second annular gap that extends circumferentially around said inner tube and said outer tube second section and the first annular gap having a width that is greater than the width of the second annular gap;

a cutting member, said cutting member at least partially integral with the distal end of said inner tube and being positioned to be in registration with the opening in the distal end of said outer tube second section; and a bearing sleeve that is fitted to said inner tube and that is located over a section of said inner tube that is distal to said inner hub and proximal to the inlet bore formed in said outer tube first section, said bearing sleeve extending between said inner and outer tubes.

41. The cutting accessory of claim 40, wherein:

said inner tube has a constant outer diameter until the distal end; and said outer tube is formed so that said outer tube first and second sections each have an inner diameter and the inner diameter of said outer tube first section is greater than the inner diameter of said outer tube second section.

42. The cutting accessory of claim 40, wherein:

said inner tube has a first window located adjacent the distal end;

the second section of said outer tube extends over the distal end of said inner tube and is formed with a second window; and the inner tube has an edge surface that defines the first window and the second section of said outer tube assembly has an edge surface that defines the second window and the edge surface are collectively shaped to form said cutting member.

43. The cutting accessory of claim 40, wherein the first section of said outer tube has a first outer diameter and the second section of said outer tube has a second outer diameter, said second outer diameter being less than the first outer diameter.

44. The cutting accessory of claim 40, wherein said inner tube has a length of at least 12.0 inches.

45. The cutting accessory of claim 40, wherein said cutting member is either a shaver that is partially formed by an edge surface in the distal end of said inner tube or a bur that is attached to the distal end of said inner tube.

* * * * *

UNITED STATES PATENT AND TRADEMARK OFFICE
CERTIFICATE OF CORRECTION

PATENT NO. : 6,638,289 B1
DATED : October 28, 2003
INVENTOR(S) : Eric T. Johnson et al.

It is certified that error appears in the above-identified patent and that said Letters Patent is hereby corrected as shown below:

Column 11,
Line 39, change "number integral" to -- member integral --
Line 43, change "cutting meter" to -- cutting member --
Line 51, change "and the second" to -- the second --
Line 63, change "mentor is a bur" to -- member is a bur --

Column 12,
Line 6, change "said cutting meter" to -- said cutting member --
Line 19, change "in Bald outer tube" to -- in said outer tube --
Line 31, change "of claim 1" to -- of claim 7 --
Line 53, change "second bearing meter" to -- second bearing member --
Line 64, change "bearing meter" to -- bearing member --
Line 64, change "cutting meter" to -- cutting member --
Line 66, change "mentor is a bur" to -- member is a bur --

Column 13,
Line 6, change "apart trot each" to -- apart from each --
Line 20, change "an cuter hub" to -- an outer hub --
Line 64, change "said cuter tube" to -- said outer tube --

Column 14,
Line 15, change "outer surf ace to" to -- outer surface to --
Line 17, change "having t a proximal" to -- having: a proximal --
Line 32, change "a cutting meter" to -- a cutting member --
Line 34, change "first bearing meter" to -- first bearing member --
Line 42, change "meter being spaced" to -- member being spaced --
Line 51, change "said bearing meter" to -- said bearing member --
Line 62, change "second bearing meter" to -- second bearing member --
Line 62, change "a smooth outer" to -- a smooth walled outer --
Line 64, change "member and in" to -- member are in --
Line 65, change "second bearing meter" to -- second bearing member --
Line 66, change "member baa an" to -- member has an --

Column 15,
Line 32, change "said inner tubs" to -- said inner tube --
Line 53, change "outer hit" to -- outer hub --

UNITED STATES PATENT AND TRADEMARK OFFICE
CERTIFICATE OF CORRECTION

PATENT NO.     : 6,638,289 B1
DATED          : October 28, 2003
INVENTOR(S)    : Eric T. Johnson et al.

It is certified that error appears in the above-identified patent and that said Letters Patent is hereby corrected as shown below:

Column 16,
Line 17, change "a cutting mentor" to -- a cutting member --
Line 38, change "to f on said" to -- to form said --

Column 18,
Line 6, change "inner tub" to -- inner tube --
Line 50, change "edge surface" to -- edge surfaces --

Signed and Sealed this

Eleventh Day of May, 2004

JON W. DUDAS
*Acting Director of the United States Patent and Trademark Office*